United States Patent [19]

Frenkel

[11] Patent Number: 5,705,708
[45] Date of Patent: Jan. 6, 1998

[54] INHIBITION OF DISCOLORATION OF CUMENE HYDROPEROXIDE

[75] Inventor: Peter Frenkel, Longview, Tex.

[73] Assignee: Witco Corporation, Greenwich, Conn.

[21] Appl. No.: 717,624

[22] Filed: Sep. 23, 1996

[51] Int. Cl.$^6$ .................................................. C07C 409/10
[52] U.S. Cl. .......................... 568/559; 568/568; 568/576; 252/186.23; 252/186.28
[58] Field of Search ..................... 568/559, 568, 568/576; 252/186.23, 186.28

[56] References Cited

U.S. PATENT DOCUMENTS 5,202,498  4/1993  Elias ......................................... 568/559

FOREIGN PATENT DOCUMENTS 1032122  6/1966  United Kingdom.

Primary Examiner—C. Warren Ivy
Assistant Examiner—Jean F. Vollano
Attorney, Agent, or Firm—Scully, Scott, Murphy & Presser

[57] ABSTRACT

Discoloration of cumene hydroperoxide is reduced or inhibited by adding to the cumene hydroperoxide an effective amount on the order of 30 to 1000 ppm of a stabilizer of the formula R'C(O)OM wherein R' is alkyl, alkenyl, cycloalkyl or aryl containing 1–40 carbon atoms, or the formula $R_4NOH$ wherein each R is independently alkyl or cycloalkyl containing 1–40 carbon atoms.

32 Claims, No Drawings

INHIBITION OF DISCOLORATION OF CUMENE HYDROPEROXIDE

FIELD OF THE INVENTION

The present invention is directed to the treatment of cumene hydroperoxide, a useful initiator for the polymerization of olefins, to prevent or reduce the undesirable discoloration over time which cumene hydroperoxide has been known to undergo.

BACKGROUND OF THE INVENTION

A significant problem in the manufacture of cumene hydroperoxide is the undesirable discoloration, from clear to a yellowish appearance, which this product has been known to undergo. According to published literature in the past, the chemical mechanism by which this discoloration occurs is not well understood; the components which cause the discoloration are not readily identified; and the factors which could avoid the discoloration have not been clearly identified.

An ideal solution to the problem would be to provide a built-in mechanism to prevent or at least inhibit the discoloration under the handling and storage conditions which are normally encountered.

U.S. Pat. No. 5,202,498 discloses that sodium hydroxide has been used to inhibit the onset of undesirable color change in cumene hydroperoxide. However, sodium hydroxide is hazardous and difficult to handle, especially when used as an aqueous solution, so a less hazardous material which reduces discoloration of cumene hydroxide would be desirable.

The present invention improves on the prior art in that it provides a more effective method for reducing discoloration of cumene hydroperoxide, and does so in a very straightforward manner.

BRIEF SUMMARY OF THE INVENTION

One aspect of the present invention is methods of treating cumene hydroperoxide which has become discolored, to reduce the degree of discoloration. Another aspect of the present invention is methods of treating cumene hydroperoxide which has not yet undergone discoloration, to retard or prevent the onset of discoloration.

The present invention is further directed to compositions which comprise cumene hydroperoxide and an effective amount of a color stabilizer which is one or more alkali metal salts of an organic acid containing 1 to 40 carbon atoms, or one or more tetraalkyl quaternary ammonium hydroxides, in an amount which inhibits or reduces the discoloration of cumene hydroperoxide.

More particularly, the present invention is directed to treating cumene hydroperoxide by adding to it a stabilizer which can be (a) one or more alkali metal salts of organic acids, the salts having the general formula R'C(O)OM (I) wherein R' is an alkyl, alkenyl, cycloalkyl or aryl group containing 1 to 40 carbon atoms and preferably 1 to 20 carbon atoms, and M is an alkali metal, i.e. sodium, potassium, rubidium or cesium; or (b) one or more quaternary ammonium hydroxides of the general formula $R_4$ NOH (II) wherein each R is the same or different and each is a branched or unbranched alkyl or cycloalkyl group containing 1 to 40 carbon atoms and preferably 1 to 4 carbon atoms.

DETAILED DESCRIPTION OF THE INVENTION

The present invention is useful in treating cumene hydroperoxide (also referred to herein as CHP) which has become discolored; such CHP is often referred to as aged. The present invention is also useful in treating CHP which has undergone little or no discoloration, such as fleshly made CHP.

One group of color stabilizers useful in this invention is compounds of the aforementioned formula (I):

$$R'C(O)OM \qquad (I)$$

In formula (I), R' is an alkyl, alkenyl, cycloalkyl or aryl group containing 1 to 40 carbon atoms and more preferably 1 to 20 carbon atoms. With respect to both formula (I) and formula (II), the term "alkyl" refers to branched and unbranched alkyl groups. The term "alkenyl" refers to branched and unbranched groups containing one or more carbon-carbon double bond. The maximum number of such bonds is dictated by the number of carbon atoms present, as is well known; preferred alkenyl groups contain one or two such bonds. The term "cycloalkyl" refers to cyclic aliphatic groups attached to the —C(O)OM moiety directly or through an alkyl bridge, and to any such groups which are alkyl-substituted. The term "aryl" refers to monocyclic and bicyclic aromatic ring systems which are bonded to the —C(O)OM moiety directly or through an alkyl bridge, and to such groups which are alkyl-substituted.

Examples of alkali metal salts of formula (I) which are useful in the present invention include sodium acetate, potassium acetate, rubidium acetate, cesium acetate, sodium methacrylate, sodium butyrate, potassium benzoate, potassium stearate, sodium stearate, and sodium propionate. A preferred embodiment is potassium acetate, and a particularly preferred embodiment of this is the addition of a 70 wt. % aqueous solution of potassium acetate to, for instance, freshly prepared CHP to provide 50–100 ppm of potassium acetate. The effectiveness of this embodiment even without the heating described below is shown in Table 5.

The amount of alkali metal salt of formula (I) that is added to cumene hydroperoxide, and that is present therein, in accordance with the present invention, is an amount effective to achieve the desired objective of decreasing or inhibiting undesirable discoloration of the cumene hydroperoxide.

To prevent or retard discoloration of CHP that is not discolored, such as freshly prepared CHP, the amount of alkali metal salt of formula (I) to add is generally at least 30 ppm (this and all amounts are in parts by weight of the CHP), and preferably on the order of 50 to 100 ppm. To reduce discoloration of CHP that has become discolored, such as aged CHP (thus also preventing or retarding the onset of further discoloration), the amount of alkali metal salt of formula (I) to add is higher, generally up to 500 ppm or even up to 1000 ppm. The upper limit is governed by practical considerations, familiar to those of skill in this art, based upon the color intensity of CHP at the time the alkali metal salt is added.

The alkali metal salt can either be added to the CHP directly and mixed until the salt dissolves, or a solution of the salt can be prepared in a mutually suitable solvent and then added to the CHP and mixed until dissolved. Examples of suitable solvents include water and alcohols.

Addition of the salt can be effective when carried out at ambient temperatures, or at moderately elevated temperatures. In a preferred embodiment, heating the mixture of CHP and the salt to 50°–70° C. for 0.5 to 2.0 hours accelerates the beneficial effectiveness of the salt in reducing or retarding undesired discoloration of the CHP.

Another group of color stabilizers useful in the present invention is quaternary ammonium hydroxides of the formula (II):

$$R_4NOH \qquad (II)$$

in which each R substituent is the same or different, and each is an alkyl or cycloalkyl group containing 1 to 40 carbon atoms and preferably 1 to 4 carbon atoms. Reference is made to the above definitions of the terms "alkyl" and "cycloalkyl".

Examples of quaternary ammonium hydroxides useful in the present invention include tetramethylammonium hydroxide, tetraethylammonium hydroxide, tetrapropylammonium hydroxide, and tetrabutylammonium hydroxide.

The amount of quaternary ammonium hydroxide of formula (II) that is added to cumene hydroperoxide, and that is present therein, in accordance with the present invention, is an amount effective to achieve the desired objective of decreasing or inhibiting undesirable discoloration of the cumene hydroperoxide.

To prevent or retard discoloration of CHP that is not discolored, such as freshly prepared CHP, the amount of quaternary ammonium hydroxide of formula (II) to add is generally at least 30 ppm, and preferably on the order of 50 to 100 ppm. To reduce discoloration of CHP that has become discolored, such as aged CHP (thus also preventing or retarding the onset of further discoloration), the amount of the compound(s) of formula (II) to add is higher, generally up to 500 ppm or even up to 1000 ppm. The upper limit is governed by practical considerations, familiar to those of skill in this art, based upon the color intensity of CHP at the time the quaternary ammonium hydroxide of formula (II) is added.

The quaternary ammonium hydroxide can either be added to the CHP directly and mixed until the ammonium compound dissolves, or a solution of the ammonium compound can be prepared in a mutually suitable solvent and then added to the CHP and mixed until the composition becomes homogeneous. Examples of suitable solvents include water and alcohols.

Addition of the quaternary ammonium hydroxide can be effective when carried out at ambient temperatures, or at moderately elevated temperatures. In a preferred embodiment, heating the mixture of CHP and the quaternary ammonium hydroxide to 50°–70° C. for 0.5 to 2.0 hours accelerates the beneficial effectiveness of the quaternary ammonium hydroxide in reducing or retarding undesired discoloration of the CHP.

The following examples are intended to illustrate the claimed invention and not to limit its scope. Numerous additional embodiments within the scope and spirit of the claimed invention will be apparent to those skilled in this art.

The following abbreviations used in the examples and tables herein have the following meanings: NaOAc, sodium acetate; KOAc, potassium acetate; CHP, cumene hydroperoxide; RbOAc, rubidium acetate; CsOAc, cesium acetate; TBAH, tetrabutylammonium hydroxide.

Analytical Method

The color intensity of the CHP compositions in the following examples was measured according to the APHA Platinum-Cobalt Standard Method using a Hach DR/2000 Spectrophotometer equipped with 25 ml matched cells at wavelength $\lambda=455$ nm. The color intensity is expressed in PtCo color units.

EXAMPLE I

This example demonstrates the beneficial effect of adding an alkali metal acetate in accordance with this invention to aged, discolored CHP.

In some runs, solid alkali metal acetate was added to the CHP, and the mixture was stirred until the acetate was dissolved. In other runs, NaOAc or KOAc were added as aqueous solutions having concentrations of 30 wt. % and 70 wt. %, respectively. Samples for reference were also run which contained no salt, and which contained sodium hydroxide as representative of the prior art. Each sample was stored for a total of 33 days. The color intensity was measured 5, 12, 19, 26 and 33 days after addition of the salts to the samples.

The amounts of salts added to the CHP, and the results obtained, are shown in Table 1. The color intensity for the sample without any added salt stayed relatively high over time. The samples containing alkali metal acetate in accordance with the present invention showed reduction of discoloration even after 5 days, and the discoloration continued to lessen with time. The results clearly show the effectiveness of the present invention.

TABLE 1

| | Color Intensity of Aged CHP in Presence of Acetates (Ac) of Alkali Metals at Ambient Temperature | | | | | | |
|---|---|---|---|---|---|---|---|
| | Wt. of Pure Additive, ppm | Ratio, mmol/100 g CHP | Color Intensity After Storing for X days, PtCo Color Units | | | | Color Change per ppm |
| | | | 5 | 12 | 19 | 26 | 33 | |
| Solid Additives | | | | | | | | |
| None | — | — | 226 | 226 | 235 | 235 | 235 | — |
| NaOAc | 460 | 0.56 | 219 | 155 | 114 | 89 | 78 | 0.32 |
| KOAc | 66 | 0.06 | 209 | 155 | 138 | 129 | 125 | 1.53 |
| KOAc | 126 | 0.13 | 185 | 141 | 122 | 112 | 105 | 0.96 |
| KOAc | 280 | 0.29 | 161 | 122 | 95 | 83 | 74 | 0.54 |
| KOAc | 540 | 0.55 | 122 | 70 | 50 | 42 | 36 | 0.35 |

TABLE 1-continued

| | Wt. of Pure Additive, ppm | Ratio, mmol/100 g CHP | Color Intensity After Storing for X days, PtCo Color Units | | | | | Color Change per ppm |
|---|---|---|---|---|---|---|---|---|
| | | | 5 | 12 | 19 | 26 | 33 | |
| RbOAc | 460 | 0.32 | 150 | 75 | 54 | 43 | 42 | 0.40 |
| CsOAc | 500 | 0.26 | 151 | 103 | 80 | 69 | 60 | 0.33 |
| NaOH | 100 | 0.25 | 186 | 145 | 123 | 114 | 106 | 1.20 |
| Aqueous Solutions of Additives | | | | | | | | |
| 30% NaOAc | 99 | 0.12 | 210 | 170 | 147 | 136 | 128 | 0.99 |
| 30% NaOAc | 198 | 0.24 | 207 | 159 | 136 | 125 | 116 | 0.56 |
| 30% NaOAc | 462 | 0.56 | 186 | 136 | 108 | 93 | 88 | 0.30 |
| 70% KOAc | 240 | 0.24 | 166 | 129 | 100 | 84 | 77 | 0.62 |
| 70% KOAc | 420 | 0.43 | 140 | 87 | 63 | 54 | 48 | 0.42 |
| 70% KOAc | 840 | 0.86 | 97 | 48 | 34 | 25 | 26 | 0.24 |

Color Intensity of Aged CHP in Presence of Acetates (Ac) of Alkali Metals at Ambient Temperature

EXAMPLE II

This example shows the effectiveness of the present invention on CHP that was slightly aged, and thus less discolored at the outset of the test than the CHP used in Example I. This example also demonstrates the effectiveness of the thermal treatment of the CHP-salt mixture.

Aqueous solutions containing NaOAc, KOAc, RbOAc, and CsOAc, (as representative of the present invention) and an aqueous solution of NaOH (as representative of the prior art) were used to introduce an alkali metal salt or hydroxide, respectively, into samples of slightly discolored CHP. Pairs of samples were prepared in each case; one member of each pair was stored at ambient temperature, and the other member of each pair was heated to 60° C. for 2 hours and then stored at ambient temperature. One sample was run without any added alkali metal compound. An initial color intensity reading was taken, followed by readings taken 1, 6, 13, 20, and 27 days later.

The amounts of additives used, and the color intensity values observed, are set forth in Table 2. All samples containing alkali metal salt in accordance with the present invention exhibited significantly lower color intensity values than the control to which no salt had been added. This reduction was apparent even after one day, and the color intensity continued to decrease thereafter. The samples which contained alkali metal salts and which had been heated prior to storage showed an even greater immediate reduction in color intensity than the corresponding samples that had not been heated. These results indicate that the heating step accelerates the reduction of discoloration of CHP.

TABLE 2

Color Intensity of Slightly Aged CHP in Presence of Acetates of Alkali Metals

| Additive | Wt. of Pure Additive, ppm | Color Intensity After Storing for X Days, PtCo Color Units | | | | | | | | | | | |
|---|---|---|---|---|---|---|---|---|---|---|---|---|---|
| | | 0 | | 1 | | 6 | | 13 | | 20 | | 27 | |
| | | A* | T** | A | T | A | T | A | T | A | T | A | T |
| None | — | 34 | | 34 | | 36 | | 42 | | 51 | | 57 | |
| 30% NaOAc | 200 | 41 | 12 | 26 | 11 | 14 | 9 | 13 | 8 | 14 | 8 | 28 | 14 |
| 70% KOAc | 50 | 35 | 10 | 18 | 8 | 10 | 7 | 8 | 7 | 4 | 8 | 3 | 8 |
| 70% KOAc | 100 | 34 | 5 | 16 | 8 | 8 | 11 | 8 | 11 | 8 | 6 | 1 | 7 |
| 70% KOAc | 200 | 33 | 5 | 14 | 7 | 7 | 8 | 6 | 8 | 5 | 10 | 0 | 10 |
| 70% RbOAc | 50 | 35 | 7 | 24 | 6 | 11 | 5 | 10 | 14 | 12 | 16 | 1 | 14 |
| 70% RbOAc | 100 | 31 | 4 | 14 | 8 | 8 | 12 | 8 | 8 | 11 | 7 | 11 | 14 |
| 70% RbOAc | 200 | 32 | 2 | 13 | 5 | 6 | 8 | 5 | 9 | 5 | 11 | 9 | 10 |
| 80% CsOAc | 200 | 35 | 5 | 16 | 5 | 10 | 4 | 8 | 2 | 15 | 3 | 15 | 5 |
| 50% NaOH | 50 | 37 | 5 | 6 | 4 | 0 | 8 | 0 | 8 | 5 | 10 | 2 | 8 |

(prior art)
*A - Samples were stored at ambient temperature
**T - Samples were heated at 60° C. for 2 hours, and then stored at ambient temperature

EXAMPLE III

This example shows the effectiveness of fatty acid salts according to this invention in reducing the discoloration exhibited by slightly aged CHP.

To separate samples of the slightly aged and discolored CHP, 100 ppm of sodium stearate and 100 ppm of potassium stearate were added. A third sample of this CHP was run with no salt addition. The samples were heated at 60° C. for 2 hours, then stored at ambient temperature for 32 days. An initial color intensity reading was taken, and then additional readings were taken after 1, 4, 11, 15, 18, 25 and 32 days.

The results are shown in Table 3. The results show that in the samples to which stearate had been added, the color intensity decreased immediately and then began to increase. Even when the color intensity began increasing, it was still significantly lower than the color intensity of the untreated sample held for the same number of days. This shows that the stearates were effective in reducing the discoloration.

TABLE 3

Color Intensity of Slightly Aged CHP in Presence of Stearates

| Solid Additive | Wt. of Additive, ppm | Color Intensity After Storing for X days, PtCo Color Units | | | | | | |
|---|---|---|---|---|---|---|---|---|
| | | 0 | 1 | 4 | 11 | 18 | 25 | 32 |
| None | — | 34 | 34 | 34 | 35 | 43 | 46 | 56 |
| Na Stearate | 100 | 35 | 20 | 22 | 24 | 28 | 29 | 38 |
| K Stearate | 100 | 14 | 10 | 11 | 11 | 14 | 19 | 22 |

* Samples were heated at 60° C. for 2 hours and then stored at ambient temperature

EXAMPLE IV

This example shows the effect of potassium benzoate, sodium methacrylate, sodium propionate, and sodium butyrate, all of which are within formula (I) of the present invention, in reducing CHP discoloration. A sample of the CHP containing no added salt was also tested. Samples were prepared by dissolving solid salts in CHP at 60° C. and heating for 2 hours. The samples were stored at ambient temperature. Color intensity readings were taken at 1, 8, 15, 22 and 29 days.

The amounts of salt added and the results are shown in Table 4. The results again show initial reduction in color intensity, signifying a reduction of discoloration over time. Even when the color intensity eventually began to increase, its value at a given number of days of storage was significantly less than the color intensity of the untreated sample after storage for the same number of days.

TABLE 4

Color Intensity of Slightly Aged CHP in Presence of Miscellaneous Salts

| Solid Additives | Wt. of Additive, ppm | Color Intensity After Storing *X days, PtCo Color Units | | | | |
|---|---|---|---|---|---|---|
| | | 1 | 8 | 15 | 22 | 29 |
| None | — | 31 | 36 | 46 | 58 | 66 |
| K Benzoate | 50 | 18 | 16 | 17 | 21 | 22 |
| Na Methacrylate | 35 | 26 | 25 | 29 | 30 | 31 |
| Na Propionate | 100 | 18 | 11 | 11 | 10 | 11 |
| Na Butyrate | 100 | 19 | 16 | 15 | 17 | 18 |

*Samples were heated at 60° C. for 2 hrs. and then stored at ambient temperature

EXAMPLE V

This example shows the effectiveness of adding alkali metal salt of organic acids in accordance with the present invention to freshly prepared CHP that was not yet significantly discolored.

A 70 wt. % aqueous solution of potassium acetate (100 ppm) was added to fresh CHP and compared to fresh CHP to which no salts had been added.

These samples were held at ambient temperature and the color intensity was measured initially and after 4, 11, 18 and 24 days.

The results obtained are set forth in Table 5. The results show that adding potassium acetate in accordance with this invention achieved significant and prolonged reduction of discoloration in CHP.

TABLE 5

Color intensity of fresh CHP with and without potassium acetate

| Additive | Wt. of Pure Additive, ppm | Color intensity after storing for x days, PtCo color units | | | | |
|---|---|---|---|---|---|---|
| | | 0 | 4 | 11 | 18 | 24 |
| None | — | 7 | 10 | 13 | 16 | 18 |
| 70% KOAc | 100 | — | 3 | 3 | 4 | 6 |

EXAMPLE VI

The procedure performed in Example IV was repeated with CHP compositions to which 18, 25 and 100 ppm of TBAH had been added from a 25 wt. % solution of TBAH in methanol. The results are shown in Table 6. They show that this quaternary ammonium hydroxide caused a significant and prolonged reduction of discoloration.

TABLE 6

Color Intensity of CHP in the Presence of TBAH

| Additive | Wt. of Pure Additive, ppm | Color Intensity After Storing* for X Days, PtCo Color Units | | | | |
|---|---|---|---|---|---|---|
| | | 1 | 8 | 15 | 22 | 29 |
| None | — | 31 | 36 | 39 | 48 | 54 |
| 25% TBAH | 18 | 25 | 18 | 20 | 21 | 22 |
| 25% TBAH | 25 | 23 | 8 | 17 | 20 | 22 |
| 25% TBAH | 100 | 14 | 1 | 2 | 3 | 3 |

*Samples were heated at 60° C. for 2 hrs. and then stored at ambient temperature.

What is claimed is:

1. A composition comprising cumene hydroperoxide and a color stabilizer selected from the group consisting of (a) alkali metal salts of organic acids, having the formula (I)

$$R'C(O)OM \qquad (I)$$

and mixtures thereof, wherein R' is an alkyl, alkenyl, cycloalkyl or aryl group containing 1 to 40 carbon atoms, and M is sodium, potassium, rubidium or cesium; and (b) quaternary ammonium hydroxides having the formula (II)

$$R_4NOH \qquad (II)$$

and mixtures thereof, wherein each R is independently an alkyl or cycloalkyl group containing 1 to 40 carbon atoms;

wherein said stabilizer is present in an amount effective to inhibit discoloration of said cumene hydroperoxide.

2. A composition according to claim 1 wherein R' contains 1 to 20 carbon atoms.

3. A composition according to claim 1 wherein each R contains 1 to 4 carbon atoms.

4. A composition according to claim 1 wherein the stabilizer is selected from the group consisting of sodium acetate, potassium acetate, rubidium acetate, cesium acetate, sodium methacrylate, sodium butyrate, potassium benzoate, potassium stearate, sodium stearate, and sodium propionate.

5. A composition according to claim 1 wherein the stabilizer is potassium acetate.

6. A composition according to claim 1 wherein the stabilizer is selected from the group consisting of tetramethylammonium hydroxide, tetraethylammonium hydroxide, tetrapropylammonium hydroxide, and tetrabutylammonium hydroxide.

7. A composition according to claim 6 wherein the stabilizer is tetraethylammonium hydroxide.

8. A composition according to claim 1 wherein the amount of said stabilizer present is at least 30 ppm by weight of the cumene hydroperoxide.

9. A composition according to claim 8 wherein the amount of said stabilizer present is up to 1000 ppm by weight of the cumene hydroperoxide.

10. A composition according to claim 8 wherein the amount of said stabilizer present is up to 100 ppm by weight of the cumene hydroperoxide.

11. A method of treating discolored cumene hydroperoxide so as to reduce said discoloration, comprising adding to said cumene hydroperoxide a color stabilizer selected from the group consisting of (a) alkali metal salts of organic acids, having the formula (I)

R'C(O)OM    (I)

and mixtures thereof, wherein R' is an alkyl, alkenyl, cycloalkyl or aryl group containing 1 to 40 carbon atoms, and M is sodium, potassium, rubidium or cesium; and (b) quaternary ammonium hydroxides having the formula (II)

R₄NOH    (II)

and mixtures thereof, wherein each R is independently an alkyl or cycloalkyl group containing 1 to 40 carbon atoms;

in an amount of said stabilizer effective to reduce discoloration of said cumene hydroperoxide.

12. A method according to claim 11 wherein R' contains 1 to 20 carbon atoms.

13. A method according to claim 11 wherein each R contains 1 to 4 carbon atoms.

14. A method according to claim 11 wherein the stabilizer is selected from the group consisting of sodium acetate, potassium acetate, rubidium acetate, cesium acetate, sodium methacrylate, sodium butyrate, potassium benzoate, potassium stearate, sodium stearate, and sodium propionate.

15. A method according to claim 14 wherein the stabilizer is potassium acetate.

16. A method according to claim 11 wherein the stabilizer is selected from the group consisting of tetramethylammonium hydroxide, tetraethylammonium hydroxide, tetrapropylammonium hydroxide, and tetrabutylammonium hydroxide.

17. A method according to claim 16 wherein the stabilizer is tetraethylammonium hydroxide.

18. A method according to claim 11 wherein the amount of said stabilizer added is at least 30 ppm by weight of the cumene hydroperoxide.

19. A method according to claim 18 wherein the amount of said stabilizer added is up to 1000 ppm by weight of said cumene hydroperoxide.

20. A method according to claim 18 wherein the amount of said stabilizer added is up to 500 ppm by weight of said cumene hydroperoxide.

21. A method according to claim 11 further comprising heating the composition formed by adding said stabilizer to said cumene hydroperoxide to a temperature of 50° C. to 70° C. for 0.5 to 2.0 hours.

22. A method of treating cumene hydroperoxide so as to inhibit its discoloration, comprising adding to said cumene hydroperoxide a color stabilizer selected from the group consisting of (a) alkali metal salts of organic acids, having the formula (I)

R'C(O)OM    (I)

and mixtures thereof, wherein R' is an alkyl, alkenyl, cycloalkyl or aryl group containing 1 to 40 carbon atoms, and M is sodium, potassium, rubidium or cesium; and (b) quaternary ammonium hydroxides having the formula (II)

R₄NOH    (II)

and mixtures thereof, wherein each R is independently an alkyl or cycloalkyl group containing 1 to 40 carbon atoms;

in an amount of said stabilizer effective to inhibit discoloration of said cumene hydroperoxide.

23. A method according to claim 22 wherein R' contains 1 to 20 carbon atoms.

24. A method according to claim 22 wherein each R contains 1 to 4 carbon atoms.

25. A method according to claim 22 wherein the stabilizer is selected from the group consisting of sodium acetate, potassium acetate, rubidium acetate, cesium acetate, sodium methacrylate, sodium butyrate, potassium benzoate, potassium stearate, sodium stearate, and sodium propionate.

26. A method according to claim 25 wherein the stabilizer is potassium acetate.

27. A method according to claim 22 wherein the stabilizer is selected from the group consisting of tetramethylammonium hydroxide, tetraethylammonium hydroxide, tetrapropylammonium hydroxide, and tetrabutylammonium hydroxide.

28. A method according to claim 27 wherein the stabilizer is tetraethylammonium hydroxide.

29. A method according to claim 22 wherein the amount of said stabilizer added is at least 30 ppm by weight of the cumene hydroperoxide.

30. A method according to claim 29 wherein the amount of said stabilizer added is up to 1000 ppm by weight of said cumene hydroperoxide.

31. A method according to claim 29 wherein the amount of said stabilizer added is up to 500 ppm by weight of said cumene hydroperoxide.

32. A method according to claim 22 further comprising heating the composition formed by adding said stabilizer to said cumene hydroperoxide to a temperature of 50° C. to 70° C. for 0.5 to 2.0 hours.

* * * * *